(12) United States Patent
Velaveni et al.

(10) Patent No.: US 8,367,080 B2
(45) Date of Patent: Feb. 5, 2013

(54) PHARMACEUTICAL FORMULATION FOR USE IN HIV THERAPY

(75) Inventors: Kiran Kumar Narsaiah Velaveni, Secunderabad (IN); Sanjay Deshraj Verma, Secunderabad (IN); Akhilesh Ashok Dixit, Secunderabad (IN); Abhijit Mukund Deshmukh, Secunderabad (IN); Sanjeev Meharchand Sethi, Secunderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 0 days.

(21) Appl. No.: 13/157,579

(22) Filed: Jun. 10, 2011

(65) Prior Publication Data

US 2011/0262533 A1    Oct. 27, 2011

Related U.S. Application Data

(63) Continuation of application No. 12/310,693, filed as application No. PCT/IN2007/000382 on Aug. 31, 2007, now abandoned.

(30) Foreign Application Priority Data

Sep. 4, 2006   (IN) .......................... 1597/CHE/2006

(51) Int. Cl.
  *A61K 9/00*       (2006.01)

(52) U.S. Cl. ........................................ 424/400; 514/269
(58) Field of Classification Search ................... None
  See application file for complete search history.

(56) References Cited

U.S. PATENT DOCUMENTS

| 3,458,622 A * | 7/1969 | Hill ............................... 424/468 |
| 2005/0031696 A1* | 2/2005 | Kolhe et al. ................... 424/488 |
| 2005/0143404 A1 | 6/2005 | Rosenberg et al. |
| 2006/0121106 A1 | 6/2006 | Kerc et al. |
| 2007/0163917 A1 | 7/2007 | Friesen et al. |

OTHER PUBLICATIONS

"Ritonavir: An Extraordinary Example of Conformational Polymorphism," Bauer, J., et al., Pharmaceutical Research, 18(6): 859-866 (2001).*
Remington's Pharmaceutical Sciences, 18th edition, Gennaro A.R., Ed., Mack Pub. Co.: Easton, PA, 1990, pp. 1633-1665.
International Search Report, PCT/IN07/000382, mailed Oct. 8, 2008.

* cited by examiner

*Primary Examiner* — David J Blanchard
*Assistant Examiner* — Daniel F Coughlin
(74) *Attorney, Agent, or Firm* — Ladas & Parry LLP

(57) ABSTRACT

The invention discloses a formulation prepared by granulating at least one anti-retro viral drug and at least one pharmaceutically acceptable additive, using an organic solvent; milling the product; finally processing the milled product to form tablets or capsules.

8 Claims, 1 Drawing Sheet

PHARMACEUTICAL FORMULATION FOR USE IN HIV THERAPY

This application is a continuation of U.S. application Ser. No. 12/310,693 filed Mar. 4, 2009, now abandoned, as a national phase entry of PCT/IN2007/000382 of Aug. 31, 2007.

FIELD OF INVENTION

The present invention relates to a pharmaceutical formulation and in particular to pharmaceutical formulations for use in HIV therapy. It also discloses the processes to make the same. The invention has been developed primarily for use as a formulation to be used for treatment in HIV therapy and will be described hereinafter with reference to this application. Also disclosed is an improved bottle pack for storing the formulations. However, it will be appreciated that the invention is not limited to this particular field of use.

BACKGROUND OF THE INVENTION AND RELATED PRIOR ART

Any discussion of the prior art throughout the specification should in no way be considered as an admission that such prior art is widely known or forms part of the common general knowledge in the field.

There are multiple formulations known for use in HIV treatment therapy. The active substance Ritonavir [NORVIR soft gelatin capsule] is characterized by low aqueous solubility, a lack of bioavailability when given in the solid state, instability once in solution under ambient conditions and a metallic taste. U.S. Pat. No. 5,484,801 discloses a formulation wherein Ritonavir formulation has been optimized with respect to the vehicle, which essentially is a solvent comprising a mixture of (1) (a) a solvent selected from propylene glycol and polyethylene glycol or (b) a solvent selected from polyoxyethyleneglycerol triricinoleate, polyethylene glycol 40 hydrogenated castor oil, fractionated coconut oil, polyoxyethylene (20) sorbitan monooleate and 2-(2-ethoxyethoxy) ethanol or (c) a mixture thereof and (2) ethanol or propylene glycol to improve the bioavailability.

Whereas Kaletra® is a formulation of two HIV protease inhibitors [Lopinavir and Ritonavir] in a single formulation. Till recently, this formulation was available in a soft gel capsule, embodied in the U.S. Pat. No. 6,458,818 granted to Abbott. The patent covers a solution of Lopinavir and Ritonavir in a long chain fatty acid organic solvent. This soft gel formulation has been criticized due to stability problems and need for keeping the formulation in refrigerated condition. Abbott has now introduced a new tablet formulation for combined administration of Lopinavir and Ritonavir, instead of the previously known soft gel formulation. It has also filed patent applications related to this tablet formulation. For instance, WO2005039551 covers a combination of Lopinavir and Ritonavir in a water soluble polymer and surfactant wherein the tablet is formulated by melt extrusion process. Specifically, the disclosed process comprises following steps:
  a) preparing a mixture of combination HIV protease inhibitors, a water-soluble polymer and a surfactant,
  b) feeding the mixture in a twin screw extruder while maintaining a high temperature [133° C.] to form a homogeneous melt,
  c) feeding this melt to a calendar with counter rotating rollers to be pressed into tablets.

HIV therapy formulations need to be made in the most economical manner thereby reducing the final prices for AIDS patients across the world, especially in third world and developing countries. The above formulation and related melt extrusion process on account of its requiring expensive extrusion machinery & use of multiple surfactants [N Vinyl pyrrolidone and Sorbitan monolaureate or polyoxyethyleneglycerol oxystearate] may not necessarily result in an economical formulation. Also, since the disclosed process requires heating the drug constituents to high temperatures [exceeding 100° C.] it may possibly result in degradation of the drug constituents.

OBJECTS OF THE INVENTION

It is an object of the present invention to overcome or ameliorate at least one of the disadvantages of the prior art, or to provide a useful alternative.

It is an object of the invention in its preferred form to provide an economical formulation for administration of at least one anti-retro viral drug.

It is an object of the invention in its preferred form to provide an economical formulation for administration of a plurality of anti-retro viral drugs in a single formulation.

It is an object of the invention in its preferred form to provide an economical formulation for administration of a plurality of protease inhibitors in a single formulation.

It is an object of the invention in its preferred form to provide an economical formulation for administration of Lopinavir and Ritonavir in a single formulation.

It is another object of the invention to provide a formulation which does not require use of expensive melt extrusion equipment.

It is another object of the invention to provide a formulation which does not require heating the drug constituents and thereby reduce chances of degradation of the drug constituents.

It is a further object of the invention to provide an improved bottle pack for storing the formulations wherein the desiccant is packed within the closure of the bottle.

SUMMARY OF THE INVENTION

According to the invention there is provided a pharmaceutical formulation for use in HIV therapy. According to one aspect of the invention there is also provided a process to make the same.

As presently contemplated, in one broad form, the invention provides a process to make a pharmaceutical formulation comprising the following steps:
a. granulating at least one anti-retro viral drug and at least one pharmaceutically acceptable additive such as a solubilizing agent, using an organic solvent;
b. milling product of step [a];
c. compressing milled product of step [b] into tablets or filling it into capsules.

Another aspect of the invention provides for a pharmaceutical formulation prepared by a process disclosed above.

As presently contemplated, in another broad form the invention provides a process to make a pharmaceutical formulation comprising the following steps:
a. granulating a plurality of anti-retro viral drugs and at least one pharmaceutically acceptable additive such as a solubilizing agent, using an organic solvent;
b. milling the granules so formed;
c. processing the milled product into pharmaceutical formulations such as tablets or capsules.

Another aspect of the invention provides for a pharmaceutical formulation prepared by a process disclosed above.

Another aspect of the invention provides for process to make pharmaceutical formulation comprising the steps of:
a) mixing a plurality of anti-retro viral drugs with pharmaceutical additives such as a solubilizing agent in an organic solvent;
b) mixing a glidant and a muco-adhesive excipients in a solvent;
c) mixing product of step [a] and [b]
d) drying product of step [c];
e) milling product of step [d];
f) processing the milled product into pharmaceutical formulations such as tablets or capsules.

Another aspect of the invention provides for a pharmaceutical formulation prepared by a process described above.

BRIEF DESCRIPTION OF THE DRAWINGS

A preferred embodiment of one the aspects of the invention, i.e. the bottle pack for packing anti retro viral formulations will now be described, by way of example only, with reference to the accompanying drawings in which:

FIG. 1 is a cross section view of a closure of the bottle pack according to the invention, while

In FIG. 1, closure [2] has a receptacle [3] for holding a desiccant [4] within closure itself. Here the receptacle [3] is a distinct part that is attached/fixed to the closure [2].

Figure 1:
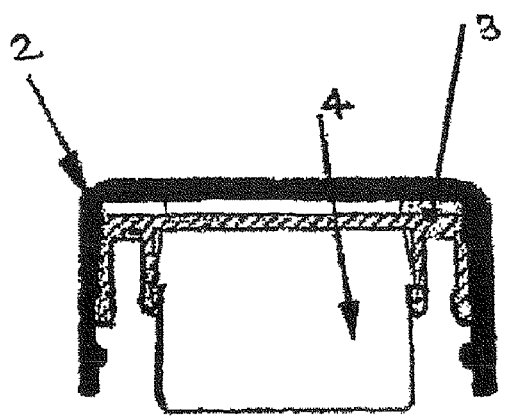
Figure 1A:
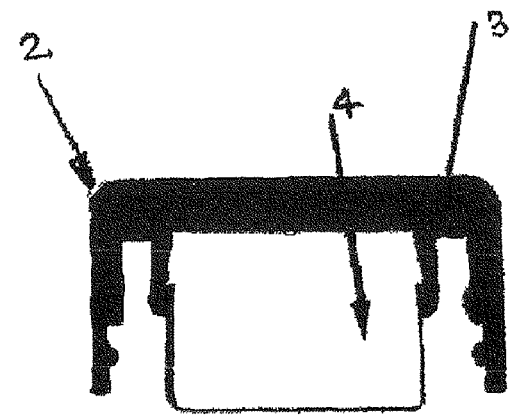
FIG. 1A shows a cross section view of an alternative closure of the bottle pack.

While in the embodiment in FIG. 1A, the receptacle [3] is molded within the closure [2] itself such that it is a permanent part of the closure body.

DETAILED DESCRIPTION INCLUDING PREFERRED EMBODIMENTS OF THE INVENTION

The bioavailability of drugs is directly related to their dissolution in the gastro-intestinal fluids. The anti retro viral drug may be selected from HIV protease inhibitor[s] such as Lopinavir, Ritonavir, Saquinavir, Nelfinavir, Atazanavir, Indinavir, Tipranavir, Palinavir, Amprenavir, Fosemaprenavir & Darunavir etc. Also, other anti-retro viral drugs such as Nucleoside Reverse Transcriptase Inhibitors [NRTIs] or Non-Nucleoside Reverse Transcriptase Inhibitors [NNRTIs] can be effectively employed without undue experimentation in the present invention to render a stable and economical formulation. For e.g. Nucleoside Reverse Transcriptase Inhibitors could be selected from Abacavir, Didanosine, Emtricitabine, Lamivudine, Stavudine, Zidovudine & Zalcitabine. Similarly, NNRTIs could be selected from Nevirapine, Delavirdine or Efavirenz. Also, Nucleotide Reverse Transcriptase Inhibitors such as Tenofovir could also be employed. The preferred single drug is Ritonavir.

Thus, even a combination of any of the above anti-retro viral drugs and at least one pharmaceutically acceptable additive granulated in an organic solvent subsequently milled, and subsequently processed to pharmaceutical formulations such as tablets or capsules would also come within the ambit of the process of present invention. The preferred drug combination is Lopinavir:Ritonavir in a proportion of 4:1.

Formulation methods such as melt extrusion, spray drying and solvent evaporation with melt extrusion have been suggested to make tablet formulations of Lopinavir and Ritonavir combination. These methods need specialized equipment and heating at high temperatures.

The present invention avoids factors such as use of specialised melt extrusion equipment, processing at high temperatures and provides a stable, solid pharmaceutical dosage form comprising at least one protease inhibitor admixed with pharmaceutical additives, granulated in an organic solvent, milled and finally processing the milled product into pharmaceutical formulations such as tablets or capsules. Thus, using wet granulation manufacturing process and standard equipment a novel, stable and economical formulation for delivering at least one anti-retro viral drug is disclosed. The formulation may also consist of a plurality of HIV protease inhibitors. The process of granulation is carried out in presence of an organic solvent. The process sequence consists broadly of:

a) Mixing at least one anti-retro viral drug with an organic solvent and a pharmaceutical additives, preferably a solubilizer;
b) Mixing and sifting excipients[s] and then adding them to an organic solvent, preferably the same as used in step [a]. The excipients can be one that has muco-adhesive property such as HPMC along with more excipients such as a glidant for e.g. colloidal silicon dioxide;
c) Mixing the above two to form a uniform thick paste;
d) Drying the paste using vacuum or nitrogen stream or heat;
e) Milling the above dried mass;
f) Optionally, adding lubricants to the milled mixture.
g) This milled product can be compressed into tablets or filled in capsules.

It is to be noted that all the steps [a] and [b] can be combined, such that all the items are mixed in the organic solvent to form a paste. Also, instead of one drug, more than one drug can also be mixed in step [a]. The process may be is carried out in a Nitrogen atmosphere.

Examples have been provided that will clarify the above general process steps.

The solvents to be used are organic solvents such as methanol, dichloromethane, ethanol, acetone, ethyl acetate, isopropyl alcohol, preferably, dichloromethane.

The term 'pharmaceutically acceptable additive' includes 'pharmaceutically acceptable excipient' within its ambit and the singular term includes plural as well. Pharmaceutically acceptable additives such as a solubilizing agent or a combination of solubilizing agents, pharmaceutically acceptable excipients having muco-adhesive properties, a glidant, a lubricant and a disintegrating agent can be added to further enhance the properties of the formulation. The solubilizing agent may be either a pharmaceutically acceptable polymer or a pharmaceutically acceptable copolymer or any pharmaceutically acceptable fatty acid ester, used singly or in combination and should ideally be dispersible or soluble in organic solvent selected. Examples of solubilizing agents are glyceryl mono-oleate, polyethylene-polypropylene glycol copolymer [Poloaxamer], sorbitan esters, polyoxyl castor oil, polyoxyethylene stearates. Commercially available substances such as Poloaxamer 124/407 can also serve as the solubilizing agent. The pharmaceutically acceptable excipient having muco-adhesive properties include cellulose ethers, polyacrylic acid, polymethacrylates, poloxamer, polydextrose, copovidone, polyvinyl alcohol, chitosan, guar gum, sodium alginate, dextrin, polyethylene glycol etc. An e.g. for excipient having muco-adhesive property is Hydroxypropylmethyl cellulose [HPMC, commercially available as Hypromellose].

Glidants improve the flowability of the powder making up the tablet during production. Glidants can be selected from selected from the group consisting of: silicon dioxide, colloidal silicon dioxide, fumed silicon dioxide, sodium aluminosilicate, calcium silicate, powdered cellulose, microcrystalline cellulose, corn starch, sodium benzoate, calcium carbonate, magnesium carbonate, asbestos free talc, metallic stearates, calcium stearate, magnesium stearate, zinc stearate, stearowet C, starch, starch 1500, magnesium lauryl sulfate, or magnesium oxide, where colloidal silicon dioxide is the preferred glidant.

Lubricants may be selected from the group of magnesium stearate, calcium stearate, sodium stearyl fumarate, stearic acid, hydrogenated cottonseed oil, sodium benzoate, sodium lauryl sulfate etc.

Skilled professionals will appreciate that although the examples disclosed below involve use of rapid mixer granulator, alternative equipments like planetary mixers, ribbon blender etc. can also be employed without any undue experimentation to get the desired results. Although the invention has been described with reference to specific examples, it will be appreciated by those skilled in the art that the invention may be embodied in other forms.

In one aspect of the invention, the pharmaceutical dosage form comprises:
a) from about 5 to about 30% by weight of the total dosage form (preferably from about 10 to about 25% by weight of the total dosage form) of at least one anti-retro viral drug;
b) from about 10 to about 40% by weight of the total dosage form (preferably from about 10 to about 25% by weight of the total dosage form) of a solubilizing agent (or any combination of thereof)
c) from about 3 to about 70% by weight of the total dosage form (preferably from about 50 to about 65% by weight of the total dosage form) of a muco-adhesive excipient (or any combination of thereof)
d) quantities of lubricants and glidants are to be added using conventional knowledge.
d) solvent for granulation is also added in terms of standard wet granulation parameters.

The milled product post granulation is processed further, for e.g. it can be compressed to form tablets or filled into capsules, using standard machines/processes, known to persons skilled in the art.

In its preferred form, the process involves:
a) mixing lopinavir and ritonavir and at least one solubilizing agent, in the presence of an organic solvent;
b) mixing a polymer and glidant in an organic solvent;
c) mixing the products of step [a] and [b] to form a uniform paste;
d) drying the paste;
e) milling the dried product;
f) processing the milled product into pharmaceutical formulations such as tablets or capsules.

The formulations of the present invention can be stored in ordinary HDPE/plastic bottles. However, we have disclosed an improved bottle pack for storing such formulations. Normal bottles have a closure with a cavity that closes around the bottle's neck such that the neck of the bottle fits within the closure's cavity. When medicines are stored in bottles, a desiccant is also added to absorb moisture. But this practice means an additional processing step on the packing line as also the risk that some patients may ingest the desiccant confusing it with medicine.

Our improved bottle pack consists of a bottle and a closure that has a receptacle within its cavity such that the receptacle holds the desiccant. The closure is fitted by the bottle pack supplier with a desiccant within the receptacle and hence there is no need for putting in a desiccant at the time of filling the medicines. The receptacle may be formed as a part of the closure itself or it may be attached/added inside the closure. The receptacle may fixed within the closure or it may be removably fixed within the closure. FIG. 1 illustrates a closure where the receptacle is added inside the closure, while FIG. 1A illustrates a closure where the receptacle is a part of the closure body itself.

Such a closure with a pre-fitted desiccant has the following advantages:
a) The desiccant in the top portion of the bottle helps in capturing all the moisture in the head space much faster as moisture is vaporizing in an upward direction.
In a normal bottle where the desiccant sachet is put inside along with the pharmaceutical product, it absorbs the moisture whenever moisture settles down.
b) Different quantities of desiccant can be fixed within the receptacle without changing the bottle/closure dimensions.
c) The present closure eliminates one extra operation of inserting the desiccant on machine and also reduced inventory, reduced storage space as this desiccant i.e. pre-filled inside the closures.

Example 1

Wet Granulation Process

| Ingredient | % w/w |
| --- | --- |
| Lopinavir | 20.0 |
| Ritonavir | 5.0 |
| Poloxamer 124 | 12.0 |
| Hypromellose (6 cps) | 58.0 |
| Colloidal silicon dioxide | 3.0 |
| Sodium stearyl fumarate | 2.0 |
| Dichloromethane | q.s. |

Manufacturing Steps:
a. Lopinavir, Ritonavir and Poloxamer 124 were dissolved in dichloromethane;
b. Colloidal silicon dioxide and hypromellose were sifted through a size 20 mesh;
c. The mixture from step [b] was loaded into a rapid mixer granulator;
d. The drug mixture of step [a] was added to the granulator and processed;
e. The product was dried under vacuum at about 40° C.;
f. The dry product was then milled in a multimill;
g. Sodium lauryl sulfate was mixed with milled product and sifted for about 10 minutes;
h. This sifted product was finally compressed into tablets.

Example 2

| Ingredient | % w/w |
| --- | --- |
| Lopinavir | 20.0 |
| Ritonavir | 5.0 |
| Glyceryl mono-oleate | 4.0 |
| Poloxamer 407 | 63.0 |
| Colloidal silicon dioxide | 5.0 |
| Sodium stearyl fumarate | 2.0 |
| Talc | 1.0 |
| Methanol | q.s. |

Manufacturing Steps:
a. Lopinavir, Ritonavir and glyceryl mono-oleate were dissolved in methanol;

b. Colloidal silicon dioxide and Poloxamer 407 were sifted through a size 20 mesh;
c. The mixture from step [b] was loaded into a rapid mixer granulator;
d. The drug solution of step [a] was added to the granulator and processed;
e. The product was dried under vacuum at about 40° C.;
f. The dry product was then milled in a multimill;
g. Sodium lauryl sulfate and talc was mixed with milled product and sifted for about 10 minutes;
h. This sifted product was finally compressed into tablets.

Example 3

| Ingredient | % w/w |
|---|---|
| Lopinavir | 15.0 |
| Ritonavir | 3.75 |
| Glyceryl monooleate | 5.0 |
| Poloxamer 407 | 15.0 |
| Hypromellose (3 cps) | 55.25 |
| Colloidal silicon dioxide | 3.0 |
| Hydrogenated cottonseed oil | 2.0 |
| Sodium lauryl sulfate | 1.0 |
| Methanol | q.s. |

Manufacturing Steps:
a. Lopinavir, Ritonavir and glyceryl monooleate were dissolved in methanol;
b. Colloidal silicon dioxide and hypromellose were sifted through a size 20 mesh;
c. The mixture from step [b] was loaded into a rapid mixer granulator;
d. The drug solution of step [a] was added to the granulator and processed;
e. The product was dried under vacuum at about 45° C.;
f. The dry product was then milled in a multimill;
g. Sodium lauryl sulfate and hydrogenated cottonseed oil was mixed with milled product and sifted for about 10 minutes;
h. This sifted product was finally compressed into tablets.

Example 4

| Ingredient | % w/w |
|---|---|
| Lopinavir | 22.0 |
| Ritonavir | 5.5 |
| Sorbitan laureate | 10.0 |
| Poloxamer 407 | 56.5 |
| Colloidal silicon dioxide | 3.0 |
| Sodium stearyl fumarate | 3.0 |
| Ethyl acetate | q.s. |

Manufacturing Steps:
a. Lopinavir, Ritonavir and sorbitan laureate were dissolved in ethyl acetate;
b. Colloidal silicon dioxide and Poloxamer 407 were sifted through a size 20 mesh;
c. The mixture from step [b] was loaded into a rapid mixer granulator;
d. The drug solution of step [a] was added to the granulator and processed;
e. The product was dried under vacuum at about 45° C.;
f. The dry product was then milled in a multimill;
g. Sodium lauryl sulfate was mixed with milled product and sifted for about 10 minutes;
h. This sifted product was finally compressed into tablets.

Example 5

| Ingredient | % w/w |
|---|---|
| Lopinavir | 16.4 |
| Ritonavir | 4.1 |
| Sorbitan laurate | 6.8 |
| Copovidone | 70.1 |
| Colloidal silicon dioxide | 1.6 |
| Sodium stearyl fumarate | 1.0 |
| Ethyl acetate | q.s. |

Manufacturing Steps:
a. Lopinavir, Ritonavir and sorbitan laurate were dissolved in ethyl acetate;
b. Colloidal silicon dioxide and Copovidone were sifted through a size 20 mesh;
c. The mixture from step [b] was loaded into a rapid mixer granulator;
d. The drug solution of step [a] was added to the granulator and processed;
e. The product was dried under vacuum at about 40° C.;
f. The dry product was then milled in a multimill;
g. Sodium stearyl sulfate was mixed with milled product and sifted for about 10 minutes;
h. This sifted product was finally compressed into tablets.

Example 6

| Ingredient | % w/w |
|---|---|
| Lopinavir | 16.4 |
| Ritonavir | 4.1 |
| Sorbitan laurate | 6.8 |
| Copovidone | 70.1 |
| Colloidal silicon dioxide | 1.6 |
| Sodium stearyl fumarate | 1.0 |
| Dichloromethane | q.s. | a. Lopinavir, Ritonavir, Sorbitan monolaurate, Copovidone and colloidal silicon were put in a rapid mix granulator and mixed;
b. Dichloromethane was added and the mixture was processed till a uniform wet mass was formed;
c. The wet mass was dried under vacuum at about 45° C.;
d. The dry product was then milled in a comminuting mill;
e. Sodium lauryl sulfate was mixed with milled product and product was finally compressed into tablets.

An alternative embodiment of the invention is disclosed below:

Example 7

| Ingredient | % w/w |
|---|---|
| Ritonavir | 10.0 |
| Poloxamer 124 | 10.0 |

-continued

| Ingredient | % w/w |
|---|---|
| Copovidone | 77.0 |
| Colloidal silicon dioxide | 2.0 |
| Sodium stearyl fumarate | 1.0 |
| Dichloromethane | q.s. | a. Ritonavir, copovidone colloidal silicon dioxide and Poloxamer 124 were put in a planetary mixer and mixed for 30 minutes
b. Dichloromethane was added and the mixture was mixed continuously till a uniform wet mass was obtained.
c. The wet mass was then removed from the planetary mixer and transferred to the tray dryer and dried at 40-50° C. preferably under vacuum.
d. The dried material was then milled using comminuting mill.
e. The sodium stearyl fumarate was mixed with milled material and finally compressed into tablets.

An alternative formulation is disclosed below:

Example 8

| Ingredient | % w/w |
|---|---|
| Ritonavir | 10.0 |
| Sorbitan monolaurate | 14.0 |
| Copovidone | 71.0 |
| Colloidal silicon dioxide | 2.0 |
| Sodium stearyl fumarate | 1.0 | a. Ritonavir, copovidone colloidal silicon dioxide and Sorbitan monolaurate were put in a jacketed vessel and mixed for 30 minutes
b. The mixture was heated with constant stirring till the mixture temperature reached the melting point of Ritonavir.
c. The heating was stopped and the material was allowed to cool down.
d. The dried material was then milled using comminuting mill.
e. The sodium stearyl fumarate was mixed with milled material and finally compressed into tablets.

Example 9

| Ingredient | % w/w |
|---|---|
| Lopinavir | 20.0 |
| Ritonavir | 5.0 |
| Poloxamer 124 | 12.0 |
| Hypromellose (6 cps) | 58.0 |
| Colloidal silicon dioxide | 3.0 |
| Sodium stearyl fumarate | 2.0 |
| Dichloromethane | q.s. | a. Lopinavir, Ritonavir and poloxamer were dissolved in dichloromethane.
b. Colloidal silicon dioxide and hypromellose were sifted through 20 mesh.
c. All the material from [b] was loaded in a Stainless steel vessel fitted with agitating device/stirrer, containing a small quantity of the solvent.
d. The product of [step c] was mixed with the drug solution [step a] in the stainless steel vessel till a uniform thick paste was formed.
e. The paste was dried at about 40° C. under vacuum [a nitrogen stream could also be used].
f. The dried mass was milled using multimill.
g. The milled granules were mixed with sodium lauryl sulfate for 10 minutes and compressed into the tablets.

Example 10

| Ingredient | % w/w |
|---|---|
| Lopinavir | 15.0 |
| Ritonavir | 3.75 |
| Glyceryl monooleate | 5.0 |
| Poloxamer 407 | 15.0 |
| Hypromellose (3 cps) | 55.25 |
| Colloidal silicon dioxide | 3.0 |
| Hydrogenated cottonseed oil | 2.0 |
| Sodium lauryl sulfate | 1.0 |
| Methanol | q.s. | a. Lopinavir, Ritonavir, poloxamer glyceryl monooleate and copovidone were dissolved in methanol.
b. The methanolic solution was then spray dried at 70° C.
c. The spray dried powder was then mixed with colloidal silicon dioxide, hydrogenated cottonseed oil and sodium lauryl sulfate for 10 minutes
d. This was then compressed into the tablets.

Example 11

| Ingredient | % w/w |
|---|---|
| Lopinavir | 16.4 |
| Ritonavir | 4.1 |
| Sorbitan laurate | 6.8 |
| Copovidone | 70.1 |
| Colloidal silicon dioxide | 1.6 |
| Sodium stearyl fumarate | 1.0 |
| Dichloromethane | q.s. | a. Lopinavir, Ritonavir and sorbitan laurate were dissolved in dichloromethane.
b. Colloidal silicon dioxide and Copovidone were sifted through 20 mesh and loaded into in a suitable stainless steel container fitted with agitating device/stirrer and containing a small quantity of the solvent.
c. The powdered blend in the stainless steel container was mixed with the drug solution till a homogeneous slurry was formed.
d. The slurry was dried at about 40° C.
e. The dried mass was milled using multimill.
f. The milled granules were mixed with sifted sodium stearyl fumarate with for 10 minutes and compress into the tablets.

We claim:
1. A process of preparing a pharmaceutical formulation, comprising the steps of:
 a. preparing a paste comprising ritonavir, copovidone, colloidal silicon dioxide and a solubilizing agent, using dichloromethane;

b. removing dichloromethane from said paste under vacuum and milling the paste to form granules;
c. lubricating said granules with a lubricant;
d. compressing said lubricated granules into tablets or filling it into capsules.

2. The process according to claim 1, wherein the lubricant is sodium stearyl fumarate.

3. The process according to claim 1, wherein the paste components of step (a) further comprises lopinavir.

4. The process according to claim 1, wherein the solubilizing agent is sorbitan laurate.

5. The process according to claim 1, wherein the solubilizing agent is glycerol monooleate.

6. The process according to claim 1, wherein the paste further comprises poloxamer or hydroxypropylmethyl cellulose.

7. The process according to claim 1, wherein the paste is prepared by mixing ritinovir, sorbitan oleate, copovidone and colloidal silicon dioxide, and subsequently granulating said mixture with dichloromethane.

8. The process of claim 1, wherein the paste is prepared by dissolving ritonavir and sorbitan laureate in dichloromethane and granulating said solution with copovidone and colloidal silicon dioxide.

* * * * *